United States Patent [19]

Woo et al.

[11] 4,450,285
[45] May 22, 1984

[54] PREPARATION OF ESTERS

[75] Inventors: Edmund P. Woo; Daniel J. Murray, both of Midland, Mich.

[73] Assignee: The Dow Chemical Company, Midland, Mich.

[21] Appl. No.: 350,853

[22] Filed: Feb. 22, 1982

[51] Int. Cl.$^3$ .............................................. C07C 67/36
[52] U.S. Cl. ...................................... 560/206; 560/97; 560/114; 560/204; 560/207; 560/232; 260/404; 260/404.5; 260/408; 260/410; 260/410.5; 260/410.9 N; 260/465 K; 260/465.9; 260/410.9 R
[58] Field of Search .......... 260/544 A, 410 C, 465 K, 260/465.9, 404, 404.5 N, 404.5 CN, 408, 410.5, 410.9 C, 410.9 N; 560/206, 207, 97, 204, 114, 232

[56] References Cited

U.S. PATENT DOCUMENTS

| 3,309,403 | 3/1967 | Mador et al. ................... 260/544 A |
| 3,338,961 | 8/1967 | Closson et al. ................. 260/544 A |
| 3,367,961 | 2/1968 | Brewbaker ......................... 560/207 |
| 3,412,114 | 11/1968 | Fernholz et al. .................... 560/206 |
| 3,457,299 | 7/1969 | Closson et al. ................. 260/544 A |

OTHER PUBLICATIONS

J. Tsuji et al., J.A.C.S. 86, 4350–4353 (1964).

Primary Examiner—Charles F. Warren
Assistant Examiner—Eugenia M. Peters
Attorney, Agent, or Firm—Douglas N. Deline

[57] ABSTRACT $\beta,\gamma$-Unsaturated esters are prepared by the reaction of the corresponding $\beta,\gamma$-unsaturated carbonate with carbon monoxide in the presence of a group VIII metal catalyst.

10 Claims, No Drawings

PREPARATION OF ESTERS

BACKGROUND OF THE INVENTION

The present invention relates to a process for preparing esters. More particularly the invention is a method of preparing $\beta,\gamma$-unsaturated esters by contacting a $\beta,\gamma$-unsaturated carbonate with carbon monoxide in the presence of a catalyst.

It is already known to carbonylate allylic chlorides, alcohols and ethers to produce the corresponding acid derivatives. J. Tsuji et al., reported in *J. Am. Chem. Soc.*, 86, 4350 (1964) that the carbonylation of allyl chloride in ethanol resulted in the formation of undesirable amounts of saturated and isomerized by-products. Even in the absence of a protonic reaction medium, W. T. Dent et al. reported in *J. Chem. Soc.*, 1588 (1964) that about 10 percent yield of the isomerized 2-butenoic chloride product was obtained.

Preparation of $\beta,\gamma$-unsaturated esters by catalyzed carbonylation of unsaturated esters has been previously taught in U.S. Pat. No. 3,367,961. The products obtained were found to be usefully employed in various industrial applications.

U.S. Pat. Nos. 3,338,961 and 3,423,456 teach a process for carbonylating alkenyl halides to form the corresponding unsaturated acid halides.

U.S. Pat. No. 4,111,856 teaches certain metal chelate catalysts. The catalysts are useful among other processes for the carbonylation of olefins to acids (column 9, line 37 and Example 2).

SUMMARY OF THE INVENTION

The present invention provides an improved process for the preparation of $\beta,\gamma$-unsaturated esters corresponding to the formula:

wherein:

$R_1$–$R_5$ independently each occurrence are selected from the group consisting of hydrogen and $R_6$; and $R_6$ is a moiety of up to about 10 carbons selected from the group consisting of alkyl, aryl, alkenyl and halo-, cyano-, nitro-, alkoxycarbonyl- or alkoxy-substituted derivatives thereof, comprising contacting a $\beta,\gamma$-unsaturated carbonate compound of the formula

wherein $R_1$–$R_6$ are as previously defined, with carbon monoxide at elevated temperatures and pressures in the presence of a group VIII metal catalyst capable of catalyzing the carbonylation reaction.

The invention provides a highly selective process for conversion of allylic carbonates into the corresponding esters. Because allylic carbonates may be prepared from allylic alcohols by known techniques, e.g., by reaction with a chloroformate, the process therefore provides a unique process to convert allylic alcohols into the corresponding esters.

Compared to prior art processes such as that of U.S. Pat. No. 3,367,961, the invented process gives high yields and reaction rates at reduced reaction temperatures and pressures. The invented process furthermore, substantially reduces the occurrences of double bond migration thereby providing more selective formation of the desired $\beta,\gamma$-unsaturated ester than heretofore possible.

DETAILED DESCRIPTION OF THE INVENTION

Allylic carbonates of the previously provided formula that may suitably be employed according to the instant invention preferably are allyl or methallyl carbonates. Exemplary compounds include allyl methyl carbonate, allyl ethyl carbonate, diallyl carbonate, methallyl methyl carbonate, methallyl ethyl carbonate, allyl methallyl carbonate, dimethallyl carbonate, 2-butenyl methyl carbonate, 2-hexenyl methyl carbonate, 4-methyl-2-pentenyl methyl carbonate, 3,7-dimethyl-2,6-octadienyl methyl carbonate, etc.

Most preferred allylic carbonates are allyl or methallyl $C_{1-4}$ alkyl carbonates, e.g., compounds wherein $R_1$, $R_2$, $R_4$ and $R_5$ are hydrogen, $R_3$ is hydrogen or methyl and $R_6$ is $C_{1-4}$ alkyl.

The group VIII metal catalysts for use according to the invention include iron, cobalt, nickel, ruthenium, rhodium, palladium, osmium, iridium and platinum catalysts capable of catalyzing the carbonylation reaction. The metals may be present in any form, e.g., as the metal, preferably deposited onto a support such as activated carbon, alumina, calcium sulfate, barium sulfate, silica, alumino silicates, alkaline earth oxides, zeolites, and mixtures thereof. The catalyst may also be present compounded with other elements, e.g., the corresponding chloride or acetate or a complex, e.g., triorganylphosphine or triorganylarsine complexes, or complexes of the metal or metal compound with polymeric ligands such as triphenylphosphine bound on a support of a copolymer of styrene and divinylbenzene.

Preferred catalysts are palladium catalysts such as tetrakis(triphenylphosphine)palladium, $\pi$-allyl palladium chloride, $\pi$-allyl palladium acetate, palladium acetate, palladium chloride, palladium acetylacetonate, diacetobis(triphenylphosphine)palladium, dichlorobis(triphenylphosphine)palladium, and dichlorobis(benzonitrile)palladium.

The catalyst is present in a catalytically effective amount, preferably from about 0.01 to about 10 mole percent based on allyl carbonate reactant. Most preferred are amounts from about 0.1 to about 2 mole percent. The ligand, where present, is preferably employed in an amount based on allyl carbonate from about 0.01 to about 30 mole percent and most preferably from about 0.03 to about 6 mole percent.

A solvent may also be present if desired as an aid when the allyl carbonate reactant is not easily handled. Suitable solvents are inert aliphatic and aromatic hydrocarbons, ethers, such as tetrahydrofuran, or a $C_{1-6}$ alkanol.

The carbonylation reaction is conducted at a temperature from about 20° C. to about 150° C., preferably from about 90° C. to about 120° C. Pressures are from about 500 psig to about 3000 psig and preferably from about 1000 psig to about 1500 psig. Reaction times vary depending on the reaction conditions and the allyl carbonate reactant, but suitably last from about 1 hour to 50 hours or more.

Having described the invention, the following examples are provided as further illustrative of the present process and are not to be construed as limiting.

EXAMPLE 1

Allyl methyl carbonate (11.6 g, 0.1 mole), palladium acetate (22.4 mg, 0.1 mmole) and triphenylphosphine (78.9 mg, 0.3 mmole) were placed in a 100-ml pressure vessel equipped with magnetic stirrer. The vessel was closed and flushed with purified $N_2$ and then charged with carbon monoxide to a pressure of 1000 psig. The vessel was heated to 100° C. while the contents were stirred. After 2 hours, the vessel was cooled to room temperature and the contents analyzed by gas chromatography. p-Diisopropylbenzene was used as standard for quantification of the product.

The result showed 10.0 g of methyl 3-butenoate had been formed. The yield was accordingly 100 percent.

EXAMPLES 2-12

The reaction conditions of Example 1 were substantially repeated employing the reactants, catalysts and conditions more particularly described in Table I. The product obtained in each instance was the corresponding ester formed by loss of the oxygen bond between the allylic radical and the carbonyl moiety.

TABLE I[1]

| Example | Carbonate | Catalyst | Solvent | Time (hr) | Carbonate Conv. (%) | Selectivity |
|---|---|---|---|---|---|---|
| 2 | allyl methyl carbonate | Pd(OAc)$_2$[2] | none | 2.0 | 100.0 | 100.0 |
| 3 | allyl ethyl carbonate | " | " | 2.5 | 84.3 | 100.0 |
| 4 | allyl ethyl carbonate | " | " | 4.5 | 100.0 | 100.0 |
| 5 | allyl ethyl carbonate | " | THF[3] | 4.5 | 100.0 | 100.0 |
| 6 | allyl ethyl carbonate | Pd(OAc)$_2$[4] | " | 5.5 | 100.0 | 100.0 |
| 7 | allyl ethyl carbonate | PdCl$_2$[5] | C$_2$H$_5$OH | 2.25 | 85.5 | 100.0 |
| 8 | 2-butenyl methyl carbonate | Pd(OAc)$_2$[2] | none | 2.0 | 25.0 | 91.3 |
| 9 | 2-butenyl methyl carbonate | " | " | 5.0 | 54.0 | 87.7 |
| 10 | 2-hexenyl ethyl carbonate | " | THF[3] | 5.0 | 38.0 | 57.0 |
| 11 | 2-hexenyl ethyl carbonate | " | " | 16.5 | 74.0 | 67.0 |
| 12 | 3,7-dimethyl-2,6-octadienyl methyl carbonate | " | " | 6.0 | 12.5 | 67.5 |

[1]All reactions were run at 100° C. and at a CO pressure of 1000 psig.
[2]Palladium acetate (0.1 mole % based on carbonate reactant + triphenylphosphine — 0.3 mole %).
[3]Tetrahydrofuran.
[4]Palladium acetate (1.0 mole % based on carbonate reactant + triphenylphosphine — 3.0 mole %).
[5]Palladium chloride (0.5 mole % based on carbonate reactant + triphenylphosphine — 0.1 mole %).

What is claimed is:

1. A process for the preparation of a $\beta,\gamma$-unsaturated ester corresponding to the formula:

$$R_1R_2C=CR_3CR_4R_5C(O)OR_6$$

wherein:
$R_1$–$R_5$ independently each occurrence are selected from the group consisting of hydrogen and $R_6$; and $R_6$ is a moiety of up to about 10 carbons selected from the group consisting of alkyl, aryl, alkenyl and halo-, cyano-, nitro-, alkoxycarbonyl- or alkoxy-substituted derivatives thereof,
which comprises contacting a $\beta,\gamma$-unsaturated carbonate compound corresponding to the formula $$R_1R_2C=CR_3CR_4R_5OC(O)OR_6,$$

wherein $R_1$–$R_6$ are as previously defined, with carbon monoxide at elevated temperatures and pressures in the presence of a metal catalyst capable of catalyzing the carbonylation reaction selected from the metals of group VIII of the Periodic Table.

2. The process of claim 1 wherein $R_1$, $R_2$, $R_4$ and $R_5$ are hydrogen and $R_3$ is hydrogen or methyl.

3. The process of claim 1 wherein $R_6$ is $C_{1-4}$ alkyl.

4. The process of claim 1 wherein the temperature is from about 20° C. to about 150° C. and the pressure is from about 500 psig to about 3000 psig.

5. The process of claim 4 wherein the temperature is from about 90° C. to about 120° C. and the pressure is from about 1000 psig to about 1500 psig.

6. The process of claim 1 wherein a solvent is additionally present.

7. The process of claim 1 wherein the catalyst additionally comprises a ligand.

8. The process of claim 1 wherein the catalyst comprises palladium.

9. The process of claim 8 wherein the catalyst comprises the triphenylphosphine complex of palladium acetate or palladium chloride.

10. The process of claim 9 wherein the $\beta,\gamma$-unsaturated carbonate is allyl methyl carbonate.

* * * * *